United States Patent [19]

Gabriel

[11] Patent Number: 5,591,136
[45] Date of Patent: Jan. 7, 1997

[54] INJECTION DEVICE

[75] Inventor: Jochen Gabriel, Stuttgart, Germany

[73] Assignee: Medico Development Investment Company, Zürich, Switzerland

[21] Appl. No.: 549,641

[22] Filed: Oct. 27, 1995

Related U.S. Application Data

[63] Continuation of Ser. No. 122,565, filed as PCT/EP92/00831, Apr. 13, 1992, abandoned.

[30] Foreign Application Priority Data

Apr. 15, 1991 [DE] Germany .................. 41 12 259.3

[51] Int. Cl.[6] ........................................... A61M 5/00
[52] U.S. Cl. .................. 604/211; 604/208; 604/224
[58] Field of Search ............. 604/207–211, 186, 604/187, 218, 220, 224, 232, 234; 222/287, 309, 325, 326, 327, 336, 340, 391, 137

[56] References Cited

U.S. PATENT DOCUMENTS

| | | | |
|---|---|---|---|
| 4,592,745 | 6/1986 | Rex et al. ............................. | 604/211 |
| 4,710,179 | 12/1987 | Haber et al. . | |
| 4,865,591 | 9/1989 | Sams ................................... | 604/211 |
| 4,973,318 | 11/1990 | Holm et al. ........................... | 604/208 |
| 5,092,842 | 3/1992 | Bechtold et al. ..................... | 604/211 |
| 5,104,380 | 4/1992 | Holman et al. ....................... | 604/211 |
| 5,112,317 | 5/1992 | Michel ................................. | 604/208 |
| 5,114,406 | 5/1992 | Gabriel et al. . | |
| 5,226,896 | 7/1993 | Harris .................................. | 604/208 |
| 5,308,340 | 5/1994 | Harris .................................. | 604/211 |

FOREIGN PATENT DOCUMENTS

| | | |
|---|---|---|
| 0058536 | 8/1982 | European Pat. Off. . |
| 0265876 | 5/1988 | European Pat. Off. . |
| 0268191 | 5/1988 | European Pat. Off. . |
| WO88-08725 | 11/1988 | WIPO . |

Primary Examiner—Corrine M. McDermott
Assistant Examiner—Ronald K. Stright, Jr.
Attorney, Agent, or Firm—Frishauf, Holtz, Goodman, Langer & Chick, P.C.

[57] ABSTRACT

A safety injection device, such as a hypodermic needle, for dispensing liquid from a cartridge in quantities determined by the length of a plunger which may be selectively adjusted in one position only of the plunger. The plunger comprises first and second threadedly connected sections cooperating with a connector which may be selectively activated when the plunger is moved into the one position to permit rotation of one plunger section relative to the other. Preferably, the adjustment position of the plunger coincides with its positions assumed in preparation of an injection stroke, with the connector preferably providing for undirectional rotation of the one plunger section.

32 Claims, 9 Drawing Sheets

INJECTION DEVICE

This application is a continuation of application Ser. No. 08/122,565, filed as PCT/EP92/00831 Apr. 13, 1992, now abandoned.

The invention relates to an injection device having a housing serving to receive liquid to be injected, having an adjustable-length plunger which is displaceable in the injection process between a first position, hereinafter called the dosage-setting position, and a second position, hereinafter called the inactive position, in order to expel liquid to be injected, and having an adjusting device for varying the effecting length of this plunger and hence for dosing the injected quantity of liquid to be injected.

BACKGROUND

An injection device of this kind is known from German Patent 36 38 984. This patent relates to a fully automatic injector with a spring system. In the known device, it is possible to vary the operative length of the plunger in all operating positions. Hence if someone plays with the device which can never be precluded—the risk arises that by turning it, he or she will change the length of the plunger, which can lead to incorrect dosages.

Another injection device of the type discussed at the outset is known from WO 88.08725. Once again, this is a fully automatic injector with a spring system, and in this known device as well it is possible to vary the effective length of the plunger in all operating positions, that is, including in the inactive position. In this device this is necessary to allow some injection liquid to be expelled in the inactive position, for monitoring purposes. However, if it is played with, for instance by children, it might be possible under some circumstances for a large amount of insulin to be expelled by mistake. This known device has the advantage that—as a result of various safety provisions—actual dose setting is not possible until the device is in its cocked position. This is achieved at the cost of relatively complicated operation.

SUMMARY OF THE INVENTION

It is therefore an object of the invention to furnish a novel injection device.

According to invention, this object is achieved by an injection device having a housing serving to receive injection liquid, having an adjustable-length plunger, which in the injection process is displaceable between a first position, hereinafter called the dosage-setting position, and a second position, hereinafter called the inactive position, in order to expel injection liquid, and having a control arrangement, which in the dosage setting position, by means of an operative connection, enables varying the effective length of the plunger and hence setting of the dosage of the quantity of injection liquid to be injected, while conversely in the inactive position, this operative connection is disabled. Accordingly, in the inactive position that the device assumes after an injection, one can play with it arbitrarily without thereby changing the set dose, because the operative connection that enables a change in the effective length of the plunger by the control arrangement is disabled in this inactive position.

This is achieved in a preferred manner by interrupting the operative connection in the inactive position. In a currently less preferred alternative, the length adjustment may be blocked in this position.

It is especially advantageous to proceed such that a blocking means is provided between the adjustable-length plunger and the housing, the blocking means enabling an axial displacement of the adjustable-length plunger relative to the housing from its inactive position into its dosage-setting position only in a certain rotational position or a certain rotational position range of this plunger. Accordingly, the injection device can be put into its dosage-setting position only at a predetermined rotary position of the adjustable-length plunger. Since dose setting is not possible until this dosage-setting position, it is thus achieved that dosing always begins from the same zero position, which is typically marked by a suitable symbol on the housing. Adjusting the dose is then done by actuating the control member up to the desired dose value, which can be read from a scale or in the usual manner counted from clicking sounds.

The injection device is preferably formed such that the blocking means is not operative in a motion of the adjustable-length plunger from its dosage-setting position into its inactive position. In this case, accordingly, this blocking means is of the kind that is operative in only one direction and does not hinder the injection process, independently of the dose set.

Particularly when this blocking means is used, the possibility is achieved in a very advantageous way of assigning the control member a stop that is operative in the dosage-setting position and that puts an upper limit on the adjustable dose. This stop may be adjustable, thereby making it possible to individually calibrate the maximum adjustable dose to suit the requirements of the patient. An upper limit can be set on the maximum dose in a very advantageous way as a result, and the physician may for instance prescribe an injection device having a predetermined maximum dose, to avert errors on the part of the patient as much as possible. Naturally, below this maximum dose, smaller dose settings continue to be possible.

A very simple feature of the invention is characterized in that the adjustable-length plunger has a threaded spindle, guided in a thread of a threaded member, with which threaded member a guide member, formed for longitudinally guiding the threaded spindle, is rotatably connected, which guide member is located axially displaceably in the housing. This makes adjusting the length of the plunger very simple and makes it possible at little expense for parts.

A highly advantageous feature of the invention is characterized in that a detent arrangement is provided between the threaded member and the guide member. The effect of this detent arrangement is that the adjustable-length plunger reliably keeps its length, set by the user, during the injection, because except in dose setting—it prevents relative rotation between the guide member and the threaded member and as a result blocks displacement of the threaded spindle out of its set position. On the other hand, this detent arrangement enables an adjustment of the effective length of the plunger in discrete increments, for instance in increments of one unit to be injected, if the device is in its active position, and in the adjustment it produces clicking noises that can be counted by the user.

A highly advantageous further feature of the invention is characterized in that the guide member is rotatable relative to the housing in the inactive position, but conversely is not rotatable relative to the housing in the dosage-setting position. As long as the guide member is in the inactive position and as a result is rotatable, no change in the effective length of the plunger—and hence dose setting—is possible. However, if the guide member is in the dosage-setting position, then it is not rotatable relative to the housing, and the dose can be set. The connection in a manner fixed against relative rotation in the dosage-setting position can be achieved in a preferred way in that the guide member is form-fittingly or non-positively connected to the housing in the dosage-setting position, and in particular one proceeds such that the guide member is provided with an indentation or a complimentary protrusion, with which a protrusion or indentation of the housing in engagement in the dosage-setting position, but not in the inactive position, as a result of which in the inactive position, for varying the effective location of the plunger, the operative connection is interrupted.

A very advantageous further feature of the invention is characterized in that the rotation between the threaded member and the guide member is limited to a direction of rotation which effects a lengthening of the effective length of the plunger. This prevents the dosage from being mistakenly done in the wrong direction, in which the effective length of the plunger would be shortened and the patient would consequently not receive any medication. Thus the patient can set a dose only in the "right" direction—in the wrong direction, the device "blocks". It is advantageously possible for the detent arrangement to be formed to block a rotation in the undesired direction of rotation. In that case, the detent arrangement enables rotation only in a single direction, which brings about an increase in the effective length of the plunger.

Further details and advantageous further features of the invention will become apparent from the exemplary embodiment described hereinafter and shown in the drawing, and to be understood in no way as a restriction of the invention. They show:

FIG. 1, a side view of an injection device according to the invention;

FIG. 2, a longitudinal section through the injection device of FIG. 1 in its inactive position, or in other words after the conclusion of an injection;

FIG. 3, a longitudinal section through the injection device of FIGS. 1 and 2 in its active position, but before a dose that is to be injected is set;

FIG. 4, a longitudinal section analogous to FIG. 3, but after the setting of the dose to be injected;

FIG. 5, a longitudinal section through the device of FIG. 4, but after the conclusion of the injection process;

FIG. 6, a perspective view of the parts of the device used for setting the dose, seen individually;

FIG. 6A shows another embodiment of part c of FIG. 6;

FIG. 7, a perspective view of the parts of the device used for setting the dose, in the assembled state and in the position analogous to FIG. 2;

FIG. 8, a perspective view analogous to FIG. 7, but in the position analogous to FIG. 4, or in other words when the dose to be injected is being set;

FIG. 9, a longitudinal section through the part of the device used for setting the dose, on a enlarged scale; and FIGS. 10–14, sections taken along the lines X—X through XIV—XIV of FIG. 9.

DETAILED DESCRIPTION

In the following description, the terms left, right, bottom, top and so forth refer to the applicable drawing figure. The terms proximal and distal are used in the usual way in medicine; that is, proximal means toward the patient and distal means away from the patient.

Figure 1:
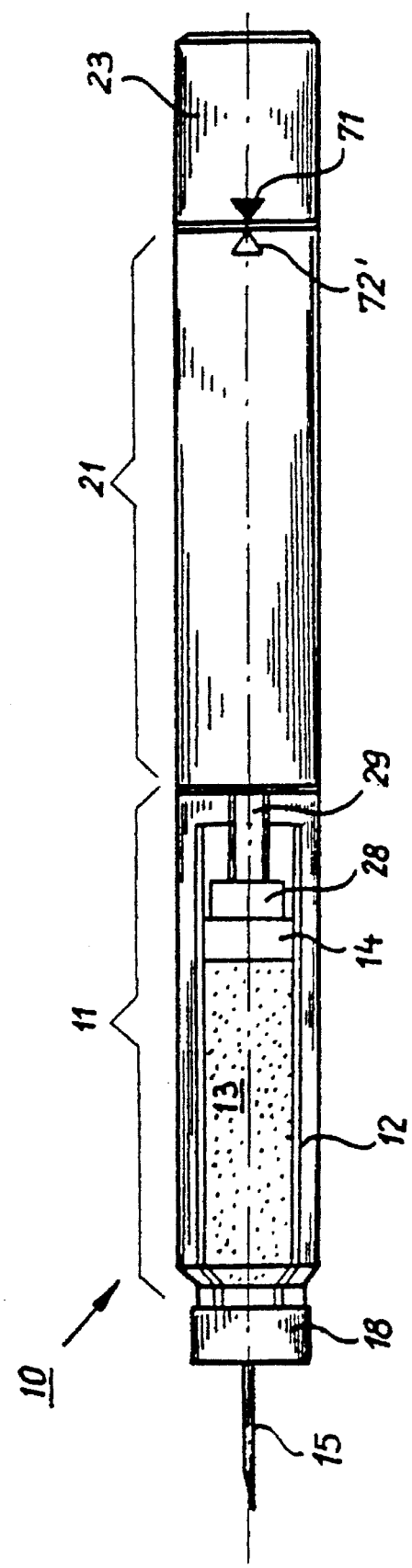

FIG. 1 shows an injection device 10 according to the invention, seen in a side view and on a scale of approximately 1:1. Its left housing part 11 is made of transparent material and contains in its interior a cartridge 12, which typically is of glass and is filled with the liquid 13 to be injected, such as papaverin or insulin. On the right in FIG. 1, this liquid is limited by a piston 14 of some suitable elastic material, typically rubber, that is displaceable in the axial direction. If this piston 14 is displaced to the left, then liquid is pressed out of the cartridge 12 and exits through an injection needle 15, also called a hollow needle. The distance by which the piston 14 is displaced to the left in an injection determines the quantity of liquid injected. The user can visually observe the location of the piston 14 through the housing part 11 and therefore knows how much injection liquid is still available.

Figure 2:
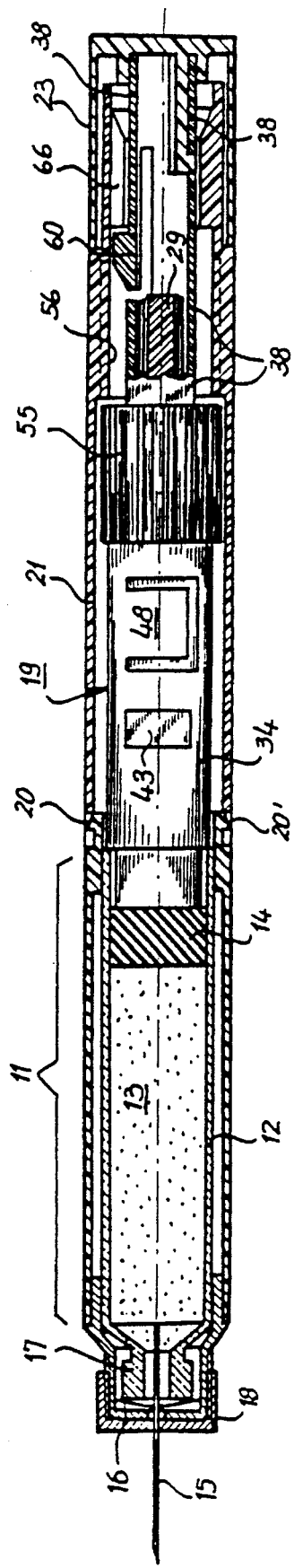

The cartridge 12, as shown in FIG. 2, tapers at its left end, where it is provided with a metal cap 17 that holds a thin rubber membrane 16. The injection needle 15 is retained in a threaded cap 18, and when this cap is screwed onto a male thread on the proximal end of the housing part 11, the distal end of the needle 15 pierces the rubber membrane 16 and penetrates into the injection liquid 13. The needle 15 can thus be easily replaced by unscrewing the thread cap 18—so that a sterile needle can be available for each injection.

The left housing part 11 is connected by detent connections 20, as shown, to a right housing part 21, which—like the left housing part 11—may be made of a suitable plastic, but in this case the plastic need not be transparent. The mechanism 19 for setting the quantity of liquid to be injected and for carrying out the actual injection process, that is, the process that follows the penetration of the tissue of the patient by the needle 15 and in which the liquid is injected into this tissue, are located in the housing part 21.

Figure 3:
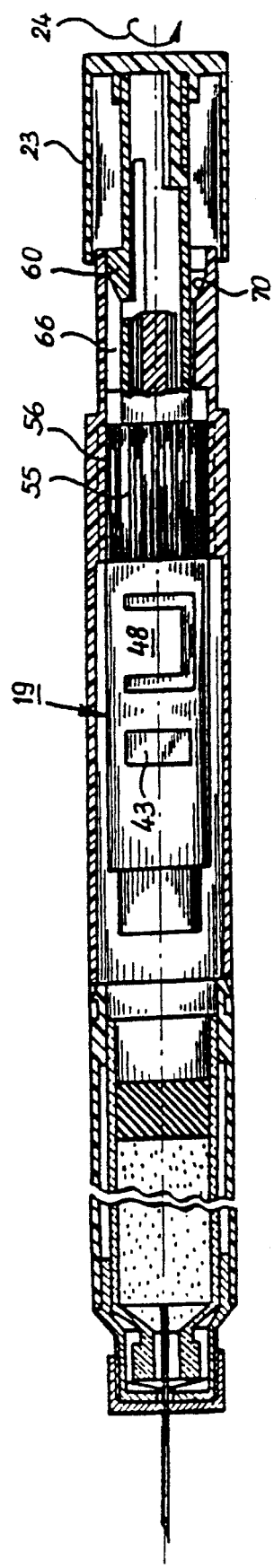

For setting the quantity of liquid to be injected and carrying out the injection process, a control member 23 is used, in the form of an actuation knob. As a comparison of FIG. 2 with FIG. 3 shows, this control member 23 can be displaced in an axial direction. It can also, in the dosage-setting position, hereinafter also called the active position, be rotated, as indicated by an arrow 24 in FIG. 3, in order to set the quantity of liquid to be injected.

Figure 6:
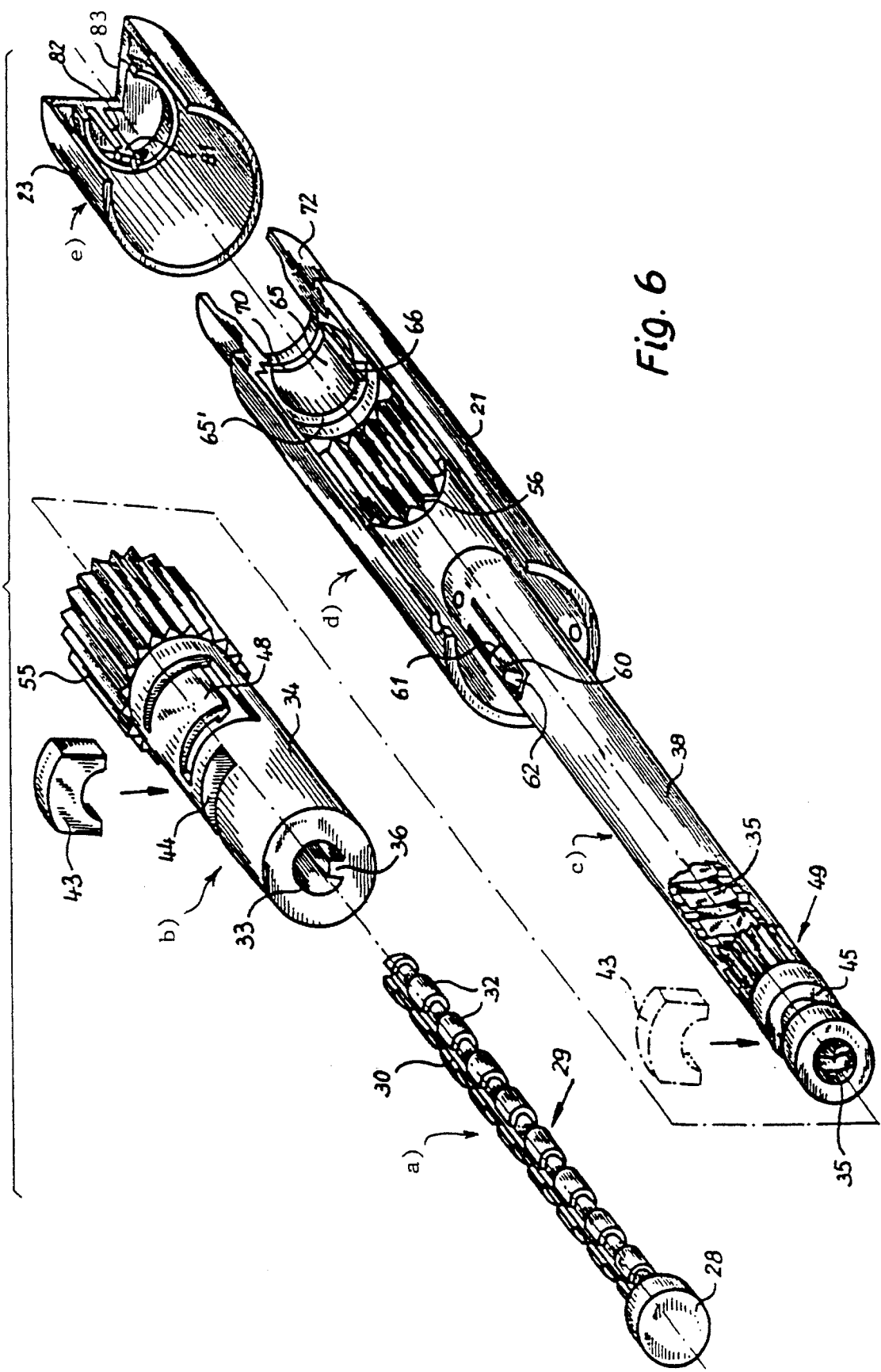
Figure 8:
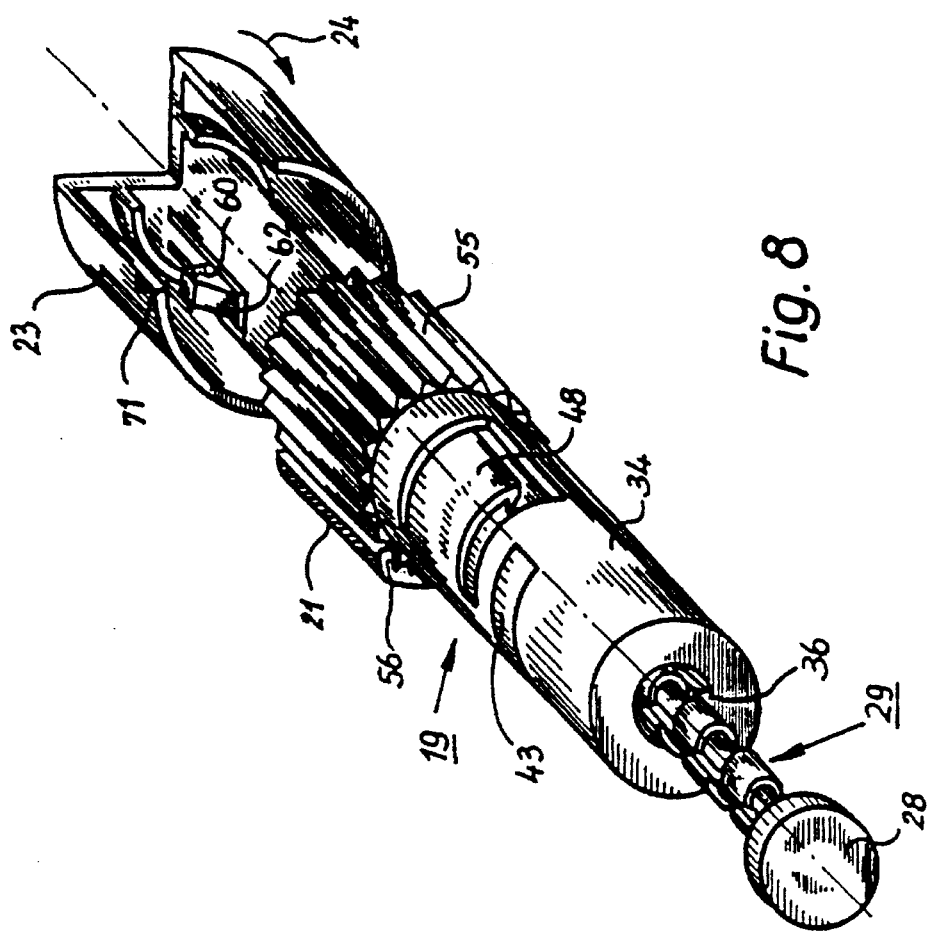
Figure 7:
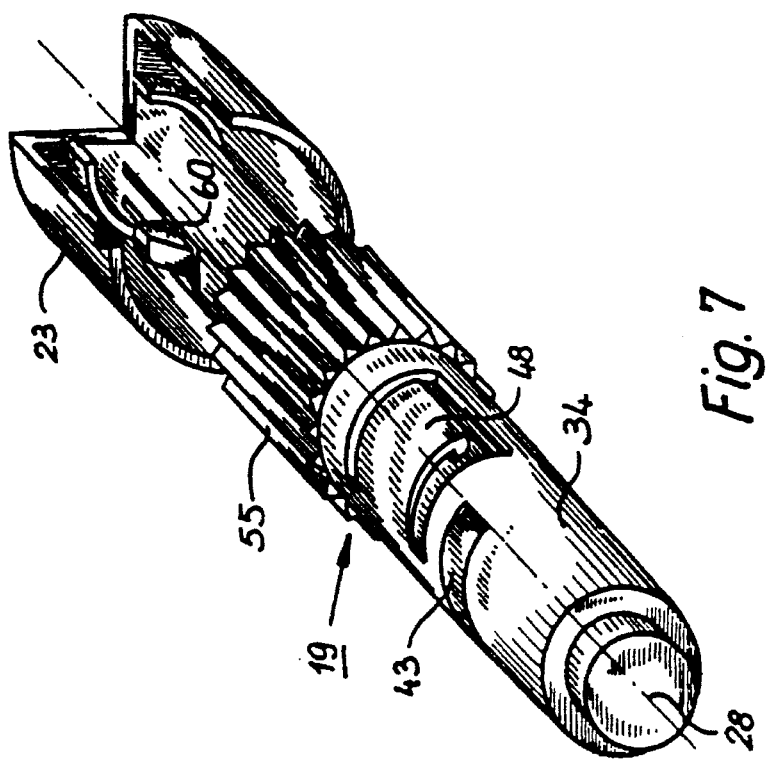

FIGS. 6–8 show the mechanism 19 and its parts in a perspective view, which is accordingly easier to understand. The mechanism 19 comprises only a few parts, which are typically inexpensively made as injection-molded parts from some suitable plastic material.

Figure 10:
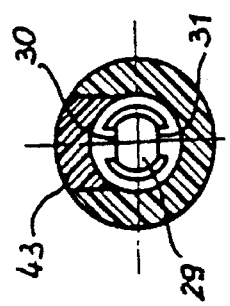

Acting directly upon the piston 14 is the proximal end 28 of a threaded spindle 29 (FIG. 6, part a), which preferably has two opposed longitudinal grooves 30, 31 (FIG. 10) and which is provided on its outside with a coarse-pitch rectangular thread 32. The threaded spindle 29 is injection molded from plastic, and the two opposed longitudinal grooves 30, 31 prevent it from warping after being removed from the injection mold, or from becoming bent, which could interfere with its function.

The threaded spindle 29 is inserted through an axial opening 33 of a guide member 34, (FIG. 6, part b) and it is guided longitudinally in this axial opening 33 by in a guide protrusion 36 that is provided there and runs in one of the longitudinal grooves 30 or 31 of the threaded spindle 29.

After being inserted through the axial opening 33, the threaded spindle 29 is screwed into the female thread 35 of a threaded member 38 see FIG. 6, part c. The latter is pulled into an axial recess 40 (FIG. 9) of the guide member 34 and, once it has reached its terminal position, is secured against axial displacement relative to the guide member 34 by a locking member 43. The locking member 43 is introduced from the outside through an opening 44 (FIG. 6, part b) of the guide member 34 and with its inner end it engages an annular groove 45 on the proximal end of the threaded member 38. Hence the threaded member 38 and the guide member 34 can be rotated relative to one another but cannot be displaced relative to one another, except for the unavoidable play in such arrangements.

Accordingly if the threaded member 38 is rotated when in its active position, as represented by an arrow 24 in FIG. 3, for dosage-setting purposes, then the threaded spindle 29 would also rotate with it. However, if the guide member 34 in the active position is locked in a nonrotatable manner in the housing part 21, then the threaded spindle 29 cannot rotate relative to the housing part 21 but instead is forced into an axial motion.

The rotation between the threaded member 38 and the guide member 34 is also limited, specifically by a detent arrangement having a detent pawl 48 on the guide member 34, which pawl engages a detent tooth system 49 on the threaded member 38. Upon assembly, this detent arrangement 48, 49 is released by raising the detent pawl 48. It then—preferentially—enables only a counterclockwise rotation of the control member 23, looking at this control member from the distal side, but blocks against a clockwise rotation. Consequently, the threaded spindle 29 can be rotated only out of the threaded member 38, together with which it forms an adjustable-length plunger 29, 38, but cannot be rotated into the threaded member 38. This length adjustment of the plunger 29, 38 is possible, however, only if the guide member 34 at that time is secured against rotation in the housing part 21.

Figure 6A:
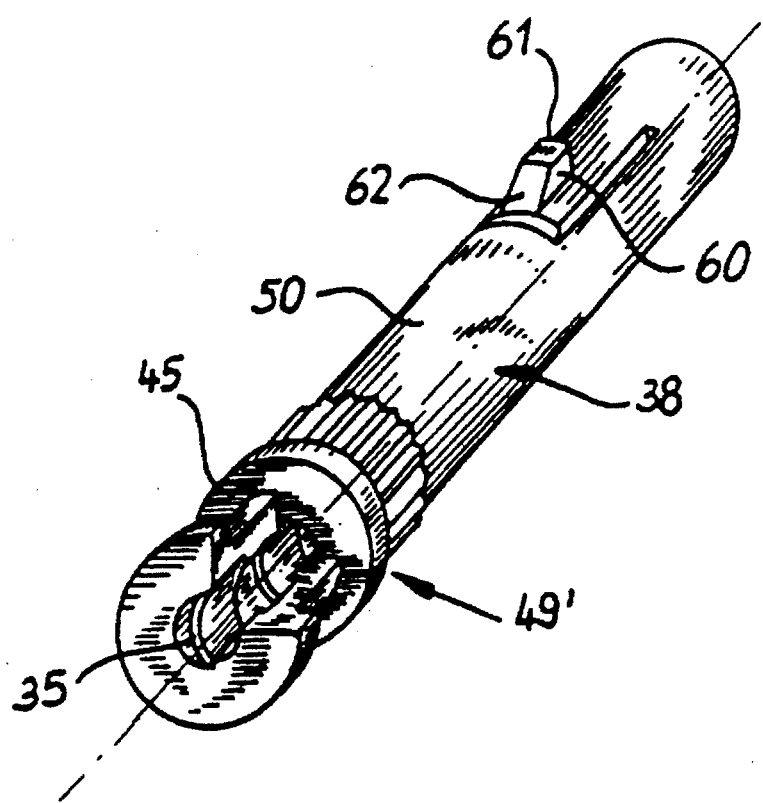
Figure 9:
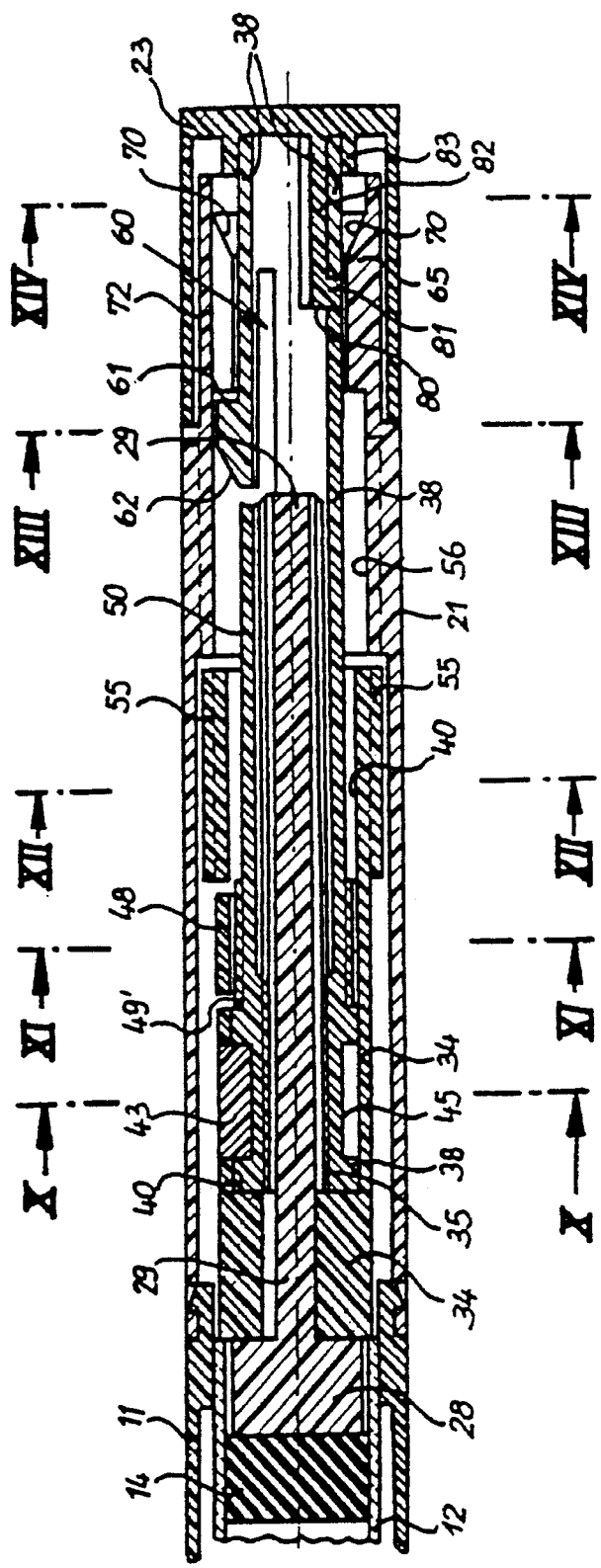

FIG. 6A shows a variant of the threaded member 38 part c of FIG. 6. The female thread 35 is shown more clearly here. The detent tooth system 49' here is formed identically to that of FIGS. 9 and 11. It enables dosage setting in both directions; that is, if the patient has set the dose of his medicine too high, he can reverse the dosage setting again somewhat, which is not possible in the version of part c of FIG. 6). The cylindrical segment 50 adjoining the tooth system 49' in the distal direction preferably has a smaller diameter than the tooth system, as shown in FIGS. 6A and 9. This makes it easier to produce the threaded member 38 as an injection molded part. Parts 45 and 60, 61, 62 of FIG. 6A are identical with part c and therefore will not be described again.

According to the invention, securing of the guide member 34 against rotation relative to the housing part 21 exists only in some of the possible axial positions of the mechanism 19; that is, the length adjustment is not possible in all positions.

To that end, in the exemplary embodiment, a system of external splines 55 is provided on the outside of the guide member 34 and on its distal end, and a corresponding system of internal splines 56 is associated with it in the interior of the housing part 21.

As FIG. 9 clearly shows, in the position after an injection, which can also be called the inactive position, the external tooth system 55 (on the guide member 34) is not in engagement with the internal tooth system 56 (in the interior of the housing part 21); that is, in this position, which is also shown in FIG. 2, a rotation of the control member 23 brings about only a rotation of the mechanism 19, including the threaded spindle and its proximal end 28, but not the unscrewing of the threaded spindle 29 out of the threaded member 38. This is important because people often unconsciously play with articles and, hence, there is a tendency to rotate this device and its parts, and because this is possible without danger in this inactive position, the setting of the device cannot be altered as a result. Adjusting the total length of the plunger 29, 38 in fact necessarily requires rotating the threaded member 38 relative to the guide member 34, which is possible only if the guide member 34 is restrained by the housing part 21. Yet this is not the case in the inactive position; that is, in the inactive position, setting of the injection dose is not possible.

On its distal end region, the threaded member 38 is provided in the manner shown with a resiliently deflectable blocking member 60, which is formed on its distal side 61 as a blocking means and on its proximal side 62 with an incline; see in particular FIG. 9.

Figure 4:
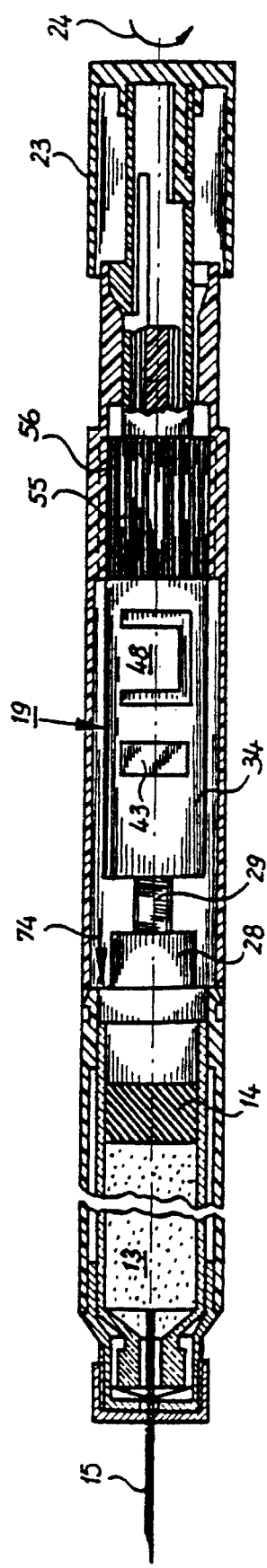

A blocking means belt 65 (FIG. 6, part d) in the interior of the distal end of the housing part 21 is associated with the blocking member 60 (FIG. 6, part c). This blocking belt 65 takes the form of a radially inwardly protruding annular bead which has an opening in the form of a longitudinal groove 66 only at one point, the cross-section shape of this groove being adapted to that of the blocking member 60. That is, only at the point of this longitudinal groove 66 can the blocking member 60 overcome the blocking belt 65, if the threaded member 38 is to be displaced out of its inactive position (FIG. 2) into its active position (FIGS. 3 and 4).

It is accordingly compulsory that the displacement of the mechanism 19 from the inactive position into the active position is possible only in a specific rotational position of this mechanism 19 relative to the housing part 21.

The longitudinal groove 66 has still another function, however, because it guides the control member 23 until the control member has reached its active position, and only then enables setting of the dose. That is, as long as the blocking member 60 is located in the longitudinal groove 66, this groove prevents any rotation of the control member 23. This forces the patient to displace the control member 23 all the way into the active position, because only then is dose setting made possible.

As FIG. 3 in fact shows particularly clearly, the blocking member 60, upon attainment of the active position, emerges from the longitudinal groove 66 and enters a frusto-conical recess 70 on the distal end of the blocking belts 65, the cone angle of which is adapted to the slope of the incline 62, so that the incline can rotate in the recess 70 and one can there, that is, after reaching the active position, set the dose by rotating the control member 23.

The device has its zero position in this position, that is, once the blocking member 60 has left the longitudinal groove 66, and in this position, a symbol 71 (FIG. 1) provided on the control member 23 may for instance be located opposite the zero position of a scale (not shown) that is provided on the outside of the distal end region 72 of the housing part 21.

In the inactive position, this distal end region 72 is covered by the control member 23 and then is not visible. In FIG. 1, a marking 72' may additionally be provided on the housing part 21. In the active position, as shown in FIGS. 3 and 4, it is possible as in FIG. 4, by rotating the control member 23 in the direction of the rotational arrow 24, to adjust the proximal end 28 of the threaded spindle 29 in the direction of the arrow 74, that is, in the proximal direction. This rotation of the control member 23 in the direction of the rotational arrow 24 is preferentially possible only up to some maximum. For this reason—including when the maximum injection dose is being set—the proximal end 28 of the threaded spindle 29 keeps an adequate distance for safety from the piston 14.

Figure 14:
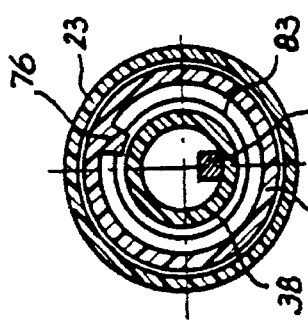
Figure 13:
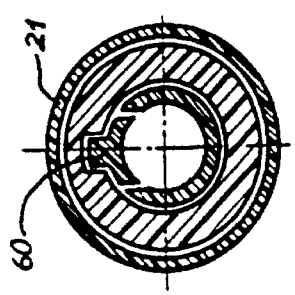
Figure 12:
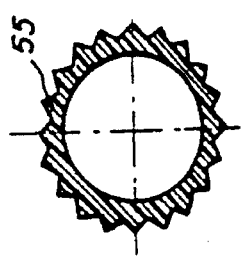

As FIG. 14 shows, a stop 76 for the blocking member 60 may be provided on the inside of the segment 72 (of the housing part 21), and this stop 76 limits the dosage to a maximum of one rotation of the control member 23, or as needed to an even smaller angular travel, for instance a one-half rotation. This prevents overdosing with certainty.

At this point, it should be noted that in the case of purely acoustical dosage setting, that is, by counting clicking noises, the arrangement can be simplified, because then the blocking member 60 and the longitudinal groove 66 can be dispensed with; but then the possibility of the stop 76 that prevents overdosage is not possible either. In that case, it is possible for the proximal end 28 of the threaded spindle 29 to be adjusted far enough that there is no longer an adequate safety distance from the piston 14. This possibility is therefore not so preferable.

In the active position, the external tooth system 55 of the guide member 34 meshes with the internal tooth system 56 of the housing part 21, as shown in FIGS. 3 and 4. Accordingly, in this position the guide member 34 is connected to the housing part 21 in a manner fixed against relative rotation.

It should be pointed out that this would be possible in the same way by means of a spur tooth system on the distal end of the guide member 34, which in the active position would then mesh with the corresponding spur tooth system, or simply a suitable internal protrusion, of the housing part 21. With such an embodiment, once again the user could set doses only in the active position. A purely force-locking connection between the guide member 34 and the housing part 21 would also suffice, which would have to be present only in the active position, for instance from suitably strong friction between these two parts, when they are in the active position. It is clear that manifold variations that produce the same function are possible here.

The control member 23 is secured to the distal end of the threaded member 38 by a snap connection. The threaded member 38 has a radial recess 80 for this purpose (FIG. 9), into which a radial protrusion 81 of a resilient axial extension 82 of the control member 23 protrudes from the inside. The control member 23 also has an annular axial extension 83 on the inside, which in the assembled state form-fittingly surrounds the distal end of the threaded member 38. In the assembly operation, the control member 23 accordingly merely has to be pressed onto the distal end of the threaded member 28, and then the radial protrusion 81 snaps into the recess 80 and brings about a firm connection between these parts. Securing of the housing part 11 to the housing part 21 is effected in a similar way by a snap connection that automatically arises when these housing parts 11, 21 are put together. This enables a very simple, inexpensive assembly.

Mode of operation

The injection device of FIG. 1 is produced by the manufacturer ready for use; that is, it comes to the user already loaded with a filled cartridge 12. The user secures a sterile needle 15 on the housing part 11 in the manner already described, puts the two markings 71, 72 (FIG. 1) opposite one another, and then pulls the actuation member 23 in the distal direction, as shown in FIG. 3. The blocking member 60 thereupon slides through the longitudinal groove 66, as also already described.

Only in the position shown in FIG. 3 is setting of the desired injection dose possible, and this is done by rotating the control member 23 to the point of the desired dose (arrow 24 in FIG. 4), whereupon the proximal end 28 of the threaded spindle 29 is displaced in the direction of the arrow 74 (FIG. 4), that is, in the direction toward the piston 14. Dose setting is possible because in the active position of FIGS. 3 and 4 the guide member 34 is not rotatable relative to the housing part 21, as has been described in detail above. FIG. 8 schematically shows how in this position the guide member 34, via its external tooth system 55, is in engagement with the internal tooth system 56 of the housing part 21, so that it cannot be rotated relative to the housing part 21.

Figure 5:
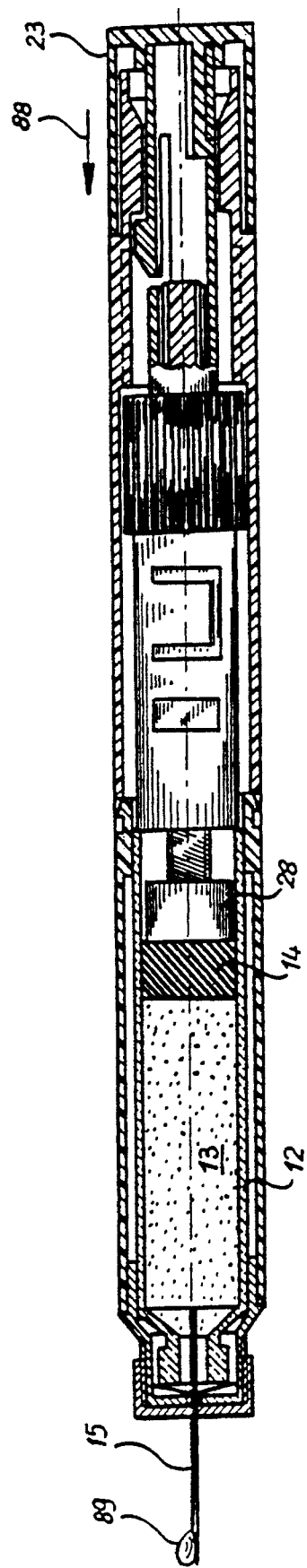

Once the required injection dose has been set, the patient then inserts the needle 15 and then presses on the control member 23 in the proximal direction (arrow 88 in FIG. 5), causing the piston 14 to be displaced in the proximal direction and causing liquid 13 to be injected through the needle 15 into the patient. This is indicated symbolically in FIG. 5 by the droplet 89. The injection is then concluded. In the injection process, the blocking member 60 is resiliently deflected radially inward by the frustoconical segment 70 on the distal end of the blocking belt 65 and slides unhindered away along the blocking means belt 65. This is not possible in the opposite direction, because then the hook-shaped side 61 of the blocking member 60 rests against a steep shoulder 65', see FIG. 6, part d, complementary to it, on the proximal end of the blocking belt 65, which prevents an axial displacement there, except for the rotational position in which the blocking member 60 can slide through the longitudinal groove 66.

The patient now again places the two symbols 71, 72 (FIG. 1) opposite one another, which can be made easier by a stop—not shown—on the proximal end of the longitudinal groove 66, and the entire process can then be repeated. A different dose setting is then possible for each injection.

In the position of FIG. 1, turning the control member 23 has no influence whatever on the injected dose, because in this position, in other words the inactive position, the guide member 34 can rotate freely relative to the housing 21, and rotation of the control member 23 therefore causes no lengthening of the plunger 29, 38. The latter merely rotates along with the control member 23.

In the position of FIG. 4, the stop 76 (FIG. 14) prevents the control member 23 from being rotated by more than one rotation and thereby sets an upper limit to the adjustable dose. The stop 76 can also be selected as needed such that it enables a rotation of the control member 23 by only half a rotation, for instance.

A special added note on the drawings: the perspective views of FIGS. 6–8 serve to explain the invention in a simple and easily understood manner. They do not match the views of FIGS. 1–5 and 9–14 in all points. The sectional views of FIGS. 2–5 and 9–14 show a functional device along with the dimensions and dimensional proportions to be observed for such a device.

Figure 11:
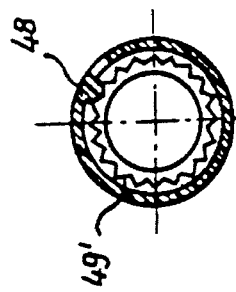

As described extensively at various points above, manifold changes and modifications are possible within the scope of the invention. It is practical for the device according to the invention to be designed as a disposable device that is thrown away after the injection liquid 13 (in the container 12) has been used up. The possibility also exists, however, after one cartridge 12 has been used, of inserting a new cartridge and screwing the threaded spindle 29 all the way back into the threaded member 38 again. In that case, the form of the detent arrangement of FIG. 11 is recommended, which enables a rotation in both directions, while the form of the detent teeth 49 in part c, as shown in FIG. 6 enables a rotation in only a single direction.

I claim:

1. An injection device for injecting adjustable dose of an injection liquid (13), comprising:

a housing (11, 21) having a space therein for receiving a container (12) having a piston (14) displaceably arranged therein and containing the injection liquid (13);

an adjustable-length plunger (29, 38) in said housing, said plunger being axially displaceable in said housing between a first dosage-setting axial position and a second axial position;

said plunger acting upon the piston (14) in the container (12) when said plunger moves from said first dosage setting axial position to said second axial position thereof;

said plunger (29, 38) comprising adjustment means for selectively adjusting the effective length of said plunger, said plunger and adjustment means including a threaded member (38);

a threaded spindle (29) guided in an interior thread (35) of said threaded member (38);

a guide member (34) rotatably connected to said threaded member;

means (30, 31, 36) arranged between said guide member and said threaded spindle (29) for axially guiding said threaded spindle and for preventing rotation of said threaded spindle relative to said guide member (34);

enabling/disabling means (55, 56) automatically enabling said adjustment means when said plunger is in said first dosage setting axial position and automatically disabling said adjustment means when said plunger is in said second axial position, said enabling/disabling means being operatively arranged between said plunger (29, 38) and said housing (11, 21) and responsive to the axial position of said plunger relative to said housing, whereby adjustment of the effective length of said plunger by said adjustment means is automatically disabled when said plunger is in said second axial position.

2. The injection device of claim 1, comprising a control member (23) coupled to said adjustable-length plunger for at least one of rotating and axially displacing said plunger.

3. The injection device of claim 2, wherein said control member is manually operable.

4. The injection device of claim 2, further comprising a stop member (76) operatively connected in said housing (22, 21) and arranged to limit rotation of said control member (23) to an extent proportional to a predetermined dose of injection fluid.

5. The injection device of claim 1, wherein said enabling/disabling means (55, 56) includes means for preventing rotation of said guide member (34) in said first position of said plunger and for enabling rotation of said guide member in said second position of said plunger.

6. The injection device of claim 5, wherein said enabling/disabling means provides, in said first position of said plunger, a force-locking connection between said housing and said guide member (34) to prevent relative rotation therebetween.

7. The injection device of claim 5, wherein said enabling/disabling means comprises one of a first and a second complementary engaging means (55, 56) provided on said guide member (34), and the other of said first and second complementary engaging means provided on said housing, said first and second complementary engaging means engaging with each other when said plunger is in the first axial position thereof.

8. The injection device of claim 1, further comprising restricting means (60, 66) arranged in said housing (11, 21) and coupled between said housing and said plunger (29, 38) for restricting axial displacement of said plunger from said second position to said first position, when said plunger is in a predetermined rotational position relative to said housing.

9. The injection device of claim 8, wherein said restricting means (60, 66) is disabled during movement of said plunger from said first position to said second position thereof.

10. The injection device of claim 1, wherein means (48, 49) is provided between said threaded member (38) and said guide member (34) for preventing unintentional relative rotation therebetween.

11. The injection device of claim 10, wherein said means for preventing said unintentional relative rotation comprises a ratchet-pawl arrangement (48, 49) coupled between said threaded member (38) and said guide member (34).

12. The injection device of claim 1, wherein said enabling/disabling means comprises rotation control means, said rotation control means, when the enabling/disabling means are in an enabled state, preventing rotation of said adjusting element relative to said housing and further comprises positional control means, controlled by the axial position of said plunger (29, 38) relative to said housing (11, 21), enabling said rotation control means when said plunger is in said first dosage setting axial position and for disabling said rotation control means when said plunger is in said second axial position, said adjusting element being freely rotatable in said housing when said plunger (29, 38) is in said second axial position.

13. The injection device of claim 1, comprising rotation limiting means provided between said threaded member (38) and said guide member (34) for limiting relative rotation therebetween to one direction.

14. An injection device for injecting an adjustable dose of an injection liquid, comprising:

a housing (11, 21) having a space therein for receiving a container (12) having a piston (14) displaceably arranged therein and containing the injection liquid (13);

setting means for setting a dose to be injected, said setting means being connected to an adjustable-length plunger (29, 38), said plunger being axially bidirectionally displaceable within said housing between a first axial position of said plunger and a second axial position of said plunger;

said plunger acting upon the piston (14) in the container;

said plunger comprising length adjustment means responsive to application of a predetermined torque thereto for adjusting the effective length of said plunger including a threaded member (38);

a threaded spindle (29) guided in an interior thread (35) of said threaded member (38);

a guide member (34) rotatably connected to said threaded member;

means (30, 31, 36) arranged between said guide member and said threaded spindle for axially guiding said threaded spindle and for preventing rotation of said threaded spindle relative to said guide member; and means (55, 56) operatively arranged between said guide member (34) and said housing and responsive to the axial position of said guide member (34) relative to said housing for preventing rotation of said guide member (34) relative to said housing in said first axial position of said plunger to enable application of a user-supplied torque between said threaded member (38) of the length adjustment means and said housing in said first position, and for enabling rotation of said guide member (34) relative to said housing in said second axial position of said plunger for automatically preventing application of the user-supplied torque between said threaded member of said length adjustment means and said housing when said plunger is in said second axial position, whereby length-adjustment of said plunger is automatically disabled when said plunger is in said second axial position.

15. The injection device of claim 14, comprising a control member (23) coupled to said adjustable-length plunger for at least one of rotating and axially displacing said plunger.

16. The injection device of claim 15, wherein said control member is manually operable.

17. The injection device of claim 15, comprising a stop member (76) operatively connected in said housing (11, 21) and arranged to limit rotation of said control member (23) to an extent proportional to a predetermined dose of injection fluid.

18. The injection device of claim 14, wherein means (48, 49) is provided between said threaded member (38) and said guide member (34) for preventing unintentional relative rotation therebetween.

19. The injection device of claim 18, wherein said means for preventing said unintentional relative rotation comprises a ratchet-pawl arrangement (48, 49) coupled between said threaded member (38) and said guide member (34).

20. The injection device of claim 14, further comprising restricting means (60, 66) arranged in said housing and coupled between said housing and said plunger for restricting axial displacement of said plunger from said second position to said first position, when said plunger is in a predetermined rotational adjustment position relative to said housing.

21. The injection device of claim 20, wherein said restricting means (60, 66) is disabled during movement of said plunger from said first axial position to said second axial position thereof.

22. The injection device of claim 14, wherein said means operatively arranged between the plunger and the housing for axially guiding the threaded spindle (29) provides, in said first position of said plunger, a force-locking connection preventing relative rotation between said housing (11, 21) and said guide member (34).

23. The injection device of claim 14, wherein said means operatively arranged between the plunger and the housing for axially guiding the threaded spindle (29) comprises a first and a second complementary engaging means (55, 56), one (55) of said engaging means being provided on said guide member (34), and the other (56) of said complementary engaging means being provided on said housing (21), said first and second complementary engaging means engaging with each other when said plunger (29, 38) is in the first axial position thereof.

24. The injection device of claim 14, comprising rotation limiting means provided between said threaded member (38) and said guide member (34) for limiting relative rotation therebetween to one direction.

25. An injection device for injecting an adjustable dose of a liquid, comprising:

a housing (11, 21) having a space therein for receiving a container (12) having a piston (14) displaceably arranged therein and containing the liquid (13);

an adjustable-length plunger (29, 38) positioned in said housing, said plunger being axially displaceable in said housing between two axial terminal positions relative to said housing, said plunger (29, 38) being axially aligned with, operatively coupled to, and acting upon the piston (14) in the container (12) upon said axial displacement thereof in a direction toward said container;

said plunger (28, 38) comprising:
 a threaded member (38),
 a threaded spindle (29) guided in an interior thread (35) of said threaded member (38),
 a guide member (34) rotatably connected to said threaded member, and
 means (30, 31, 36) arranged between said guide member and said threaded spindle for preventing rotation of said threaded spindle relative to said guide member while permitting axial movement therebetween; and means operatively arranged between said guide member (34) and said housing (11, 21) and controlled by the axial position of said plunger (29, 38) relative to said housing for establishing a torque-transferring connection between said guide member (34) and said housing in one of said terminal positions of said plunger, and for interrupting said torque-transferring connection in another one of said terminal positions of said plunger.

26. The injection device of claim 25, wherein means (48, 49) is provided between said threaded member (38) and said guide member (34) for preventing unintentional relative rotation therebetween.

27. The injection device of claim 26, wherein said means for preventing said unintentional relative rotation comprises a ratchet-pawl arrangement (48, 49) coupled between said threaded member (38) and said guide member (34).

28. The injection device of claim 25, comprising restricting means (60, 66) coupled between said housing (12, 21) and said plunger (29, 38) for restricting axial displacement of said plunger from a second terminal position of said plunger to a first terminal position of said plunger, when said plunger is in a predetermined rotational position relative to said housing.

29. The injection device of claim 28, wherein said restricting means (60, 66) is adapted to be disabled during movement of said plunger (29, 38) from said first terminal position to said second terminal position thereof.

30. The injection device of claim 25, comprising a control member (23) coupled to said adjustable-length plunger for at least one of rotating and axially displacing said plunger.

31. The injection of claim 30, wherein said control member is manually operable.

32. The injection device of claim 25, comprising rotation limiting means provided between said threaded member (38) and said guide member (34) for limiting relative rotation therebetween to one direction.

* * * * *